(12) United States Patent
Lemchen

(10) Patent No.: US 7,083,611 B2
(45) Date of Patent: Aug. 1, 2006

(54) METHOD AND APPARATUS FOR PROVIDING FACIAL REJUVENATION TREATMENTS

(75) Inventor: Marc S. Lemchen, 553 Park Ave., New York, NY (US) 10021

(73) Assignee: Marc S. Lemchen, New York, NY (US)

( * ) Notice: Subject to any disclaimer, the term of this patent is extended or adjusted under 35 U.S.C. 154(b) by 114 days.

(21) Appl. No.: 10/742,147

(22) Filed: Dec. 19, 2003

(65) Prior Publication Data
US 2005/0137584 A1 Jun. 23, 2005

(51) Int. Cl.
*A61B 18/22* (2006.01)

(52) U.S. Cl. .................... 606/9; 128/898; 607/88; 607/89

(58) Field of Classification Search ............... 128/898; 606/9
See application file for complete search history.

(56) References Cited

U.S. PATENT DOCUMENTS

| | | | |
|---|---|---|---|
| 4,813,412 A * | 3/1989 | Yamazaki et al. ............ 606/46 |
| 5,078,140 A * | 1/1992 | Kwoh ......................... 600/417 |
| 5,791,231 A * | 8/1998 | Cohn et al. ..................... 92/88 |
| 5,800,352 A * | 9/1998 | Ferre et al. ................. 600/407 |
| 5,820,623 A * | 10/1998 | Ng ................................ 606/1 |
| 5,871,018 A * | 2/1999 | Delp et al. ................... 128/898 |
| 5,879,376 A * | 3/1999 | Miller .......................... 607/89 |
| 6,246,898 B1 * | 6/2001 | Vesely et al. ............... 600/424 |
| 6,436,127 B1 * | 8/2002 | Anderson et al. ............. 607/89 |
| 6,684,129 B1 * | 1/2004 | Salisbury et al. ........... 700/245 |
| 6,786,896 B1 * | 9/2004 | Madhani et al. ............... 606/1 |
| 6,788,018 B1 * | 9/2004 | Blumenkranz ......... 318/568.11 |
| 2002/0064302 A1* | 5/2002 | Massengill ................... 382/128 |
| 2003/0208116 A1* | 11/2003 | Liang et al. ................. 600/407 |
| 2004/0162457 A1* | 8/2004 | Maggiore et al. ............. 600/1 |
| 2004/0162549 A1* | 8/2004 | Altshuler ........................ 606/9 |

* cited by examiner

*Primary Examiner*—Henry M. Johnson, III
(74) *Attorney, Agent, or Firm*—Daniel L. Dawes; Myers Dawes Andras & Sherman LLP

(57) ABSTRACT

An apparatus provides automatically controlled facial rejuvenation treatments and is comprised of a scanner for scanning a patient's face, a treatment robot, including a plurality of dermatological devices for treatment of facial skin, and a computer coupled to the scanner and robot for determining a treatment protocol of the patient's face based on a scanned input of the patient's face and for generating a plurality of commands for the treatment robot for movement and/or control of the plurality of dermatological devices for the automated treatment of the skin of the patient's face. A dermatological laser, needle injector, and/or air injector are used. The needle injector injects a minute amount of substance at a multiplicity of points within a computer-identified treatment area on the patient's face.

10 Claims, 1 Drawing Sheet

METHOD AND APPARATUS FOR PROVIDING FACIAL REJUVENATION TREATMENTS

BACKGROUND OF THE INVENTION

1. Field of the Invention

The invention relates to the field of dermatology and in particular to facial skin rejuvenation and plastic surgery.

2. Description of the Prior Art

Rubin, "Control Apparatus Particularly Useful For Controlling A Laser," U.S. Pat. No. 4,587,396 (1986) describes controlling a laser with respect to a working area to trace a desired pattern on that working area. The device traces a pattern that may be either a line pattern or an area pattern and encompasses a laser control apparatus that controls the movement of the laser beam with respect to the working area, especially the line pattern or area pattern, so as to facilitate the control of the laser for surgical applications. A desired pattern may be input manually and produces electrical signals in accordance with the input pattern; a memory stores the input pattern; display means shows the displayed pattern to an operator; and a control system directs the laser beam in a precise and predetermined manner. The system provides for automatic mode function that is linked to a verify-operation input key as a fail safe mechanism.

Slatkine et. al., "Laser Facial Rejuvenation," U.S. Pat. No. 5,807,386 (1998) and U.S. Pat. No. 5,611,795 (1997) describe a process wherein an area of skin is ablated to above the papillary dermis so as to effect permanent smoothness by use of a directed laser beam. This invention uses a laser in conjunction with a flash scanner system that contains reflectors such as mirrors or prisms to reflect laser beams of light and control the laser output to a desired pattern of irradiation. A laser beam is generated at a source 12 and travels through an optical wave guide 14 to the flash scanner 16 containing a reflector system. The optical wave guide provides superior wave guide capability for the laser beam, as well as de-focusing the laser beam; after passing through the flash scanner the laser beam is emitted to irradiate the skin surface. Use here of flash scanning enables the smoothing of raised areas of skin by vaporizing epidermal areas and underlying dermal layers layer by layer. Using laser parameters disclosed within the specification of the Patent, ablation is effected to the papillary dermal layer causing minimal dermal necrosis and thereby permitting collagen production for smoothing out the skin so as to provide sufficient healing with substantially permanent results. Rapid movement of the laser beam over the tissue is accomplished by preprogramming the desired scan time and with minimal overlapping. Slatkine fails to show any automatic detection and activation of the laser treatment to areas in need thereof.

Le Gargasson et. al., "High Resolution Device For Observing A Body," U.S. Pat. No. 6,588,900 (2003) applies a method of measuring wave front distortions within the context of identifying a shape identity or distortion according to comparison of two wave fronts. The device is further designed to detect regions of isoplanarity of a micro surface, these micro surfaces are determined by prior study over a defined surface. Working with predetermined parameters of wave front distortion the device identifies departures from this threshold wave front distortion indicating that the scanned surface is not isoplanar. It is then necessary to reduce the area of the surface until it does become isoplanar. Part of the device encompasses a stepper scanning device 30 for changing the micro surface observed. The stepper scanning device directs the optical flux emitted by the source 12 so as to scan in succession a series of micro surfaces; the extent of the surfaces analyzed is chosen by the operator. The image capture and construction device 40 encompassed within the invention is an optical-electronic receiver comprising an electronic and data processing unit provided with a clock unit that generates a sequence of events and amplifies and processes the signals coming from sensors, from possible elements for modulating the illumination flux, or from possible dynamic filtering control elements. An image construction device is placed down stream of a confocal filter and consists of a detector 700 of the photo multiplier or avalanche photo diode or CCD type. The sensor 700 is a single non-matrix sensor. The device further includes an electronic system for temporo-spatial conversion of the information making it possible, based on a single sensor, to fill in a matrix of values corresponding to the measurements carried out at each point making up the micro surface. A dynamic mask device 720 is incorporated and consists of a diaphragm spatially scanning the claimed detector so as to cover in succession the entire surface of interest.

Asah et. al., "Apparatus For Tissue Treatment," U.S. Pat. No. 6,533,776 (2003) is directed to a hand niece for cosmetic tissue treatment useful for ablating a thin epidermal layer of the skin of the patient as well as for selectively ablating lesions such as liver spots, red spots, tattoos, blood vessels, warts, hair follicles, wounds, etc. The device is designed to treat superficial tissues by laser ablation in uniform manner that is both automatic and accurate in limiting the reshaping of the surface tissues to a desired depth, causing only a minimum of damage to cells not removed. A laser beam is transmitted to the handheld device which splits the beam into first and second beams, the first beam useful for an operator to observe and confirm the area to be treated, while the second beam is the actual high energy laser beam that covers substantially the same area of treatment as the first beam. The ablating laser beam is directed through the handheld device which when held stationary provides for a automatic scanning of the desired surface to be treated. By employing a line by line traversing pattern the directed laser beam can be used to ablate areas of any arbitrary shape. Scanning is done in a non-interlacing traversing pattern to minimize or obviate tissue damage in the neighboring areas. Adaptations are contemplated for this device which include the remote operation or fine control with a distant or remote computer; various patterns of traverse of the laser beam can also be generated and accomplished through remote computer interface with the handheld scanning ablative laser device. The optics of the apparatus limits the possible areas of scanning to about 10×10 mm; obviously larger areas can be treated by sequential application of the handheld device to neighboring sections of the patient's body surface. Another interesting aspect of the clinical application of the device is that the size and shape of the scanned area can be blended into the surrounding untreated areas by use of four-sided fade-out and fade-in intensity scan lines 60. Fade-in or fade-out effects are accomplished by gradually increasing or decreasing the intensity of the laser light respectively or by decreasing or increasing the speed of the movement of the laser beam respectively. When scanning different types of tissue as a global cosmetic treatment plan envisioned by your client, it is preferred to address the speed of the scan of light beam instead of adjusting the power output of the laser beam.

Itzkan, "Laser System For Providing Target Specific Energy Deposition And Damage," U.S. Pat. No. 4,733,660 (1988) is directed to a hand piece for use with a laser that includes a scanning mechanism to control the amount of radiation applied to a target area thereby adjusting the thermal diffusion from the light absorbing portion of the target site for selective target specific energy injection or application. The invention contemplates use for dermatologic purposes and specifically incorporates an adjustable scanning mechanism to permit radiation to impinge on tissue for a predetermined amount of time to selectively necrose specific types of tissue while leaving adjacent tissue and other nearby structures undamaged. The hand tool of this invention delivers ultra short laser pulses of energy to minimize the problem of thermal diffusion which may cause unwanted tissue damage to neighboring structures. The laser radiation is transmitted to the hand tool by way of a fiberoptic cable 16 that is coupled by a cable termination 60 to a lens 62 that collimates the light along axis 54. A lens 64 with a convex surface 66 focuses the parallel light as indicated by dotted line 70 to a point 72 in FIG. 3A; the target point 72 on the surface of the skin 74 receives and absorbs the light energy. The optical axis of the lens is offset from center line 54 allowing rotation of a barrel 52 to cause the focal spot 72 to rotate on the surface of the skin 74. This device does require a cooling liquid to be introduced through tube 38 so that the liquid proceeds across the radiated areas illustrated by 76 to suction tube 40. It is important in this invention that the focal spot 72 not remain over any points of any target areas 74 for any longer than is necessary to accomplish the particular purpose intended. The scanning means of this invention is housed within the handheld device and directs the focusing automatically thereby causing the laser beam to deviate from its optical path in a systematic manner thereby moving the focused spot of laser energy at a rate and in a desired pattern within a predetermined area of the target tissue.

Wirth, "Ophthalmic Instrument Having Hartmann Wavefront Sensor Deriving Location Of Spots With Spot Fitting Techniques," U.S. Pat. No. 6,631,991 (2003) is directed to an instrument which embodies an automated surgical device for reshaping ophthalmic aberrations, in particular corneal corrections. The device includes a wavefront sensor that measures aberrations in the corneal surface by comparing light incident on the eye and reflected therefrom, allowing spatial modulation of the phase of the incident light to compensate for aberrations estimated by a wavefront center as well as a display device for graphically representing the contour aberrations. An adaptive optic subsystem is encompassed in this device and forms an image of a wavefront sensing illumination source on the retina of the eye under examination that is reflected and directed back to the instrument. An image of the reflected wavefront is created on a phase compensator and recreated at a wavefront sensor. The phase compensator operates to spatially modulate the phase of the image of the distorted wavefronts incident thereon; the wavefront sensor measures the phase aberrations in the wavefronts and operates in a closed-loop fashion with a controller to control the phase compensator so as to compensate for such phase aberrations and to restore the distorted wavefronts to phase-aligned wavefronts, which are directed to the wavefront sensor. The aberrations of the distorted wavefront measured by the wavefront sensor are deemed characteristic of the aberrations of the eye. In addition, the ophthalmic instrument of this invention preferably includes other elements seemingly in common with your concept: a headband and chin rest adjusting knob; and fixation target control knobs.

The prior art shows several systems in which the face or eye is scanned to measure topography. Computer control of a surgical laser is generally known. Feedback control of a laser used for skin treatment is shown in the art and in particular for the treatment of skin blemishes. Laser skin rejuvenation is also known.

The prior art fails however to address using a computer to calculate areas of concern in facial rejuvenation or the best way to handle each area by means of a complex of lasers, needle injectors, air injectors and spray applicators. Nor does the prior art provide a method of stabilizing the patient's head physically and with software to account for movements during the process, nor a method to be sure patient movement is accounted for.

BRIEF SUMMARY OF THE INVENTION

The invention includes an apparatus for providing automatically controlled facial rejuvenation treatments comprising a scanner for providing a scan of a patient's face, a treatment robot, including a plurality of dermatological devices for treatment of facial skin, and a computer coupled to the scanner and robot for determining a treatment protocol of the patient's face based on a scanned input of the patient's face and for generating a plurality of commands for the treatment robot for movement and/or control of the plurality of dermatological devices for the automated treatment of the skin of the patient's face.

In the illustrated embodiment the plurality of dermatological devices comprises a dermatological laser, dermatological needle injector, a dermatological air injector or any combination thereof. Other surgical and dermatological instruments or treatment devices may be added without departing from the scope and spirit of the invention, such as applicators for creams, liquids, powders.

The computer controls the dermatological needle injector to inject a substance at a multiplicity of points within a computer-identified treatment area on the patient's face, such as in a microscopic pattern of a multiplicity of injection points where a minute quantity of a dermatologically active substance is injected at each point.

The scanner and computer in combination measure and map a three dimensional facial topography including surface texture and skin color, so that wrinkles, age spots, port wine stains, birth marks, moles, tattoos, scars and other skin blemishes can be effectively and automatically treated.

The computer includes software programmed to identify areas of potential dermatological treatment on the patient's face and to determine an optimal facial treatment for each area, which can then be automatically implemented using the robot. The protocol generated by the computer may include a plurality of different types of treatments and corresponding commands to be implemented in one session or in a plurality of staged sessions. When implemented in a plurality of staged sessions, the computer is programmed to rescan the patient's face, to register the rescan with a prior stored scan of the patient's face, to compare the patient's face as rescanned with the stored scan and to modify facial dermatological treatments to be provided to the patient.

The invention also includes a method for operating and providing automated treatments using inter alia the above described apparatus.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
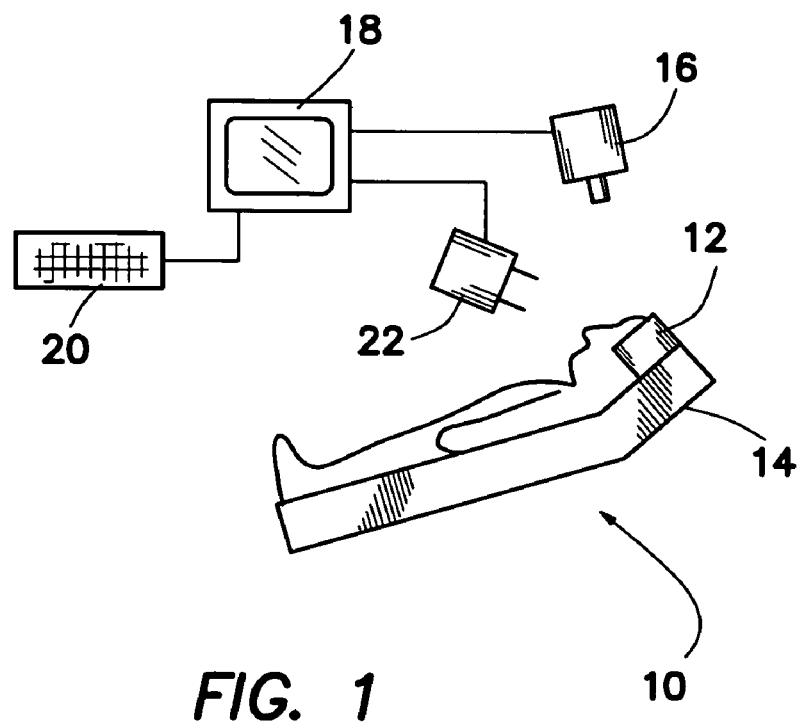
FIG. 1 is a diagrammatic block diagram of a system for facial rejuvenation devised according to the invention.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The invention is directed to a system for automatically determining and applying multiple technologies for facial skin rejuvenation, which operation has not been provided or suggested in the prior art. The invention includes a system 10, as diagrammatically shown in FIG. 1 such as a comfortably reclining chair or operating table 14 into which a patient is positioned and his or her head held relatively steady by means of a fixture or head steady rest 12. Computer 18 includes software which detects and accounts for any facial or head movements that the patient might make during treatment notwithstanding the steady rest 12. An optical scanner 16 scans the face of the patient with laser, sonic, light or any measuring system to measure and map three dimensional facial topography including surface texture and color, i.e., wrinkles, furrows, age spots etc. Such scanners 16 are well known to the art and one illustrative example used in the field of dental scanner, which could be easily adapted to facial scanning, can be found in Lemchen, et al., "Method And Apparatus For Generating Cephalometric Images," U.S. Pat. No. 5,278,756 (1994) or Le Gargasson et. al., "High Resolution Device For Observing A Body," U.S. Pat. No. 6,588,900 (2003) incorporated herein by reference.

A computer 18 coupled to scanner 16 than calculates the facial areas of concern and determines through expert algorithms the best way to dermatologically treat each facial area. In addition computer 18 is programmed to detect and adjust control for any head movement of the patient during the treatment. Any dermatological treatment and means for treatment now known or later devised is contemplated as being included within system 10. For example, a complex of lasers, needle drug injectors, and/or air injectors, collectively and symbolically denoted as treatment robot 22 is coupled to and controlled entirely by computer 18 and/or assisted by manual control by the dermatologist directly or indirectly through input device 20 coupled to computer 18, such as a keyboard, mouse, joy stick, track ball, finger or drawing (surgical) pad or any combination of the same. The use of robots 22 for delicate three dimensional movements of tools is well within the current state of the art. The dermatologist can choose to address all or some of the dermatological features and corresponding treatments at one time or establish a protocol of programmed treatments over a relatively short or an extended period of time.

The procedure starts with an air injected or topically sprayed anesthetic to numb the skin if required. A complex of lasers, needle injectors, and/or air injectors are contemplated as being included within automatically controlled treatment robot 22. Each treatment modality would be controlled according to the scanned facial map and the treatment determined by the dermatologist with the assistance of an expert software system. For example, the needles would be manipulated to inject minute quantities of dermatological drugs or treatment substances at determined points in a pattern in very closely spaced areas in a manner similar to an ink jet printer. A microscopic pattern of injection points of very minute quantities of a dermatologically active substance by means of a large number of injections with a precision and repetition, which could rarely if ever be achieved manually, can be routinely performed. Movement of the injection needle(s) are computer guided and controlled to scan over the patient's face according to the treatment protocol selected by the dermatologist. For example, topically applied "make up" to mask blemishes, moles, scars, tattoos on a temporary or semi permanent basis is also possible. In the robotic "make up" application, the selected devices or needles would begin injecting Botox to relax the appropriate areas, other needles would be used to inject collagen to fill furrows, and still another set of needles would inject restivin to smooth out the face. Lasers included with treatment robot 22 would address the age spots, if elected. Continuous scanning is performed to adjust the cosmetic application as required.

The entire procedure could be done over several visits to slowly make the changes with a computer record or protocol of the entire treatment being determined and stored. During subsequent visits the patient's face is rescanned and matched to the original scan in order to register or coordinate treatment steps. Comparison of sequential scans also serves to document and measure treatment progress between each session. In addition, depending on the nature and extent of treatment progress, the optimal treatment protocol for the patient can be modified by an expert software system to make the necessary adjustments, additions or deletions in the treatment protocol for the next step.

The approach of the invention is similar in concept in some respects to current laser eye surgery, insofar as the system takes the need for a physician out of the picture for dispensing or treatment, and allowing one physician to supervise a number of skilled technicians. What is currently considered an approximate art, which varies widely in its efficacy and nature from one practitioner to another, is converted through the judicious use of a computer to a medical science to calculate areas of concern in facial rejuvenation and to determine the best way to handle each area by means of a complex of lasers, needle injectors, and/or air injectors.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method for providing automatically controlled facial rejuvenation treatments comprising: scanning a patient's face; determining a treatment protocol of the patient's face based on a scanned input of the patient's face in a software controlled computer; generating a plurality of commands for a treatment robot for movement and/or control of a plurality of dermatological devices for the automated treatment of the skin of the patient's face; and operating the treatment robot, including a plurality of dermatological devices to treat the facial skin according to the plurality of commands.

2. The method of claim 1 where operating the treatment robot comprises selectively moving and operating a dermatological laser to effect dermatological treatment of the facial skin according to the treatment protocol determined by the computer.

3. The method of claim 1 where operating the treatment robot comprises selectively moving and operating a dermatological needle injector to effect dermatological treatment of the facial skin according to the treatment protocol determined by the computer.

4. The method of claim 1 where operating the treatment robot comprises selectively moving and operating a dermatological air injector to effect dermatological treatment of the facial skin according to the treatment protocol determined by the computer.

5. The method of claim 1 where operating the treatment robot comprises selectively moving and operating a dermatological sprayer to effect dermatological treatment of the facial skin according to the treatment protocol determined by the computer.

6. The method of claim 1 where generating a plurality of commands for a treatment robot comprises controlling a dermatological needle injector to inject a substance at a multiplicity of points within a computer-identified treatment area on the patient's face.

7. The method of claim 6 where controlling a dermatological needle injector to inject a substance at a multiplicity of points comprises injecting a minute quantity of a dermatologically active substance in a microscopic pattern at a multiplicity of injection points.

8. The method of claim 1 wherein generating a plurality of commands for a treatment robot for movement and/or control comprises generating a protocol of treatments and commands for the robot wherein the determined optimal facial treatment is automatically implemented.

9. The method of claim 8 wherein generating a protocol of treatments and commands comprises generating a protocol to be implemented in a plurality of staged sessions.

10. The method of claim 9 where generating a protocol to be implemented in a plurality of staged sessions comprises rescanning the patient's face, registering the rescan with a prior stored scan of the patient's face, comparing the patient's face as rescanned with the stored scan and modifying the facial dermatological treatments to be provided to the patient.

* * * * *